United States Patent [19]

Meyer et al.

[11] 4,455,436
[45] Jun. 19, 1984

[54] N-ACYL-O-PHENYLENEDIAMINES

[75] Inventors: Hans R. Meyer, Binningen; Max Siegrist, Lausen, both of Switzerland

[73] Assignee: Ciba-Geigy Corporation, Ardsley, N.Y.

[21] Appl. No.: 292,961

[22] Filed: Aug. 14, 1981

Related U.S. Application Data

[62] Division of Ser. No. 092,592, Nov. 8, 1979, Pat. No. 4,313,846.

[30] Foreign Application Priority Data

Nov. 20, 1978 [CH] Switzerland ................ 11883/78

[51] Int. Cl.³ ................ C07D 307/54; C07D 307/86; C07D 307/92; C07D 405/04
[52] U.S. Cl. .................... 549/467; 544/140; 544/152; 544/153; 548/374; 549/458; 549/487
[58] Field of Search ............ 548/374; 549/458, 467, 549/487; 544/153, 152, 140

[56] References Cited

U.S. PATENT DOCUMENTS

| | | | |
|---|---|---|---|
| 3,637,734 | 1/1972 | Harnisch et al. | 548/327 |
| 3,720,682 | 3/1973 | Widdig et al. | 549/487 |
| 3,869,503 | 3/1975 | Widdig et al. | 549/487 |
| 3,940,417 | 2/1976 | Schläepfer | 548/327 |
| 4,018,789 | 4/1977 | Littlewood et al. | 548/327 |
| 4,146,725 | 3/1979 | Meyer et al. | 548/327 |

FOREIGN PATENT DOCUMENTS

| | | |
|---|---|---|
| 1937029 | 2/1970 | Fed. Rep. of Germany . |
| 1576479 | 8/1969 | France . |
| 1583043 | 10/1969 | France . |
| 2290479 | 12/1978 | France . |
| 1214394 | 12/1970 | United Kingdom . |

Primary Examiner—Richard Raymond
Attorney, Agent, or Firm—Joseph G. Kolodny

[57] ABSTRACT

The invention relates to N-acyl-o-phenylenediamines of the formula

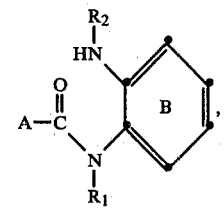

wherein A is a colorless carbocyclic or heterocyclic aromatic radical and each of $R_1$ and $R_2$ independently is an alkyl, alkenyl or phenyl radical which is unsubstituted or substituted by non-chromophoric groups, but only one of $R_1$ and $R_2$ can be phenyl, and the ring B can also be substituted by non-chromophoric groups. The invention also relates to processes for the manufacture of these compounds, their use for whitening man-made organic material their conversion into benzimidazolium compounds as well as stable, concentrated aqueous solutions of such compounds, processes for their manufacture and their use for whitening manmade organic material.

4 Claims, No Drawings

N-ACYL-O-PHENYLENEDIAMINES

This is a division of application Ser. No. 092,592 filed Nov. 8, 1979, now U.S. Pat. No. 4,313,846.

The present invention relates to novel N-acyl-o-phenylenediamines, processes for their manufacture, their use for whitening man-made organic material, a process for their conversion into benzimidazolium compounds as well as stable concentrated aqueous solutions of said benzimidazolium compounds, their manufacture and use for whitening man-made organic material.

N-acetyl-N,N'-dimethyl-o-phenylenediamine is known from "The Chemistry of Heterocyclic Compounds", Vol. 6/1, pp. 280–284. This compound, however, is unable to produce white effects.

The present invention is based on the surprising observation that specific N-acyl-N,N'-disubstituted o-phenylenediamines produce excellent white effects.

The N-acyl-o-phenylenediamines of this invention have the formula

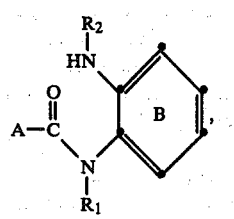
(1)

wherein A is a colourless carbocyclic or heterocyclic aromatic radical and each of $R_1$ and $R_2$ independently is an alkyl, alkenyl or phenyl radical which is unsubstituted or substituted by non-chromophoric groups, but only one of $R_1$ and $R_2$ can be phenyl, and the ring B can also be substituted by non-chromophoric groups.

Suitable carbocyclic or heterocyclic radicals A and the ring B are in particular radicals of fluorescent whitening agents of the classes of the benzofuranylbenzimidazoles (cf. U.S. Pat. Nos. 3,940,417, 4,009,994 and 4,146,725), of the phenylfuranylbenzimidazoles (cf. U.S. Pat. Nos. 3,560,485, 3,637,734 and 3,497,525; German Offenlegungsschriften Nos. 2 346 316 and 2 807 008), of the phenylpyrazolyl- or phenyltriazolylfuranylbenzimidazoles (cf. U.S. Pat. No. 4,018,789) and of the benzoxazolyl- or benzthiazolylbenzimidazoles (cf. German Offenlegungsschrift No. 2 733 439).

Non-chromophoric substituents of alkyl, alkenyl or phenyl radicals $R_1$ and $R_2$ are those found in the publications referred to above. Preferred non-chromophoric substituents are those which are resistant to alkalies and those which do not form inner salts during the treatment with alkali, such as carboxylic acid and sulfonic acid groups. Preferred substituents of alkyl and alkenyl radicals $R_1$ and $R_2$ are e.g. hydroxyl groups, alkoxy radicals of 1 to 4 carbon atoms, carbalkoxy radicals containing a total of 2 to 5 carbon atoms, cyano groups, carbamoyl radicals which are unsubstituted or substituted at the nitrogen atom by 1 or 2 alkyl groups of 1 to 3 carbon atoms, phenyl radicals which are unsubstituted or substituted by chlorine, methyl or methoxy, or dialkylamino groups containing a total of 2 to 6 carbon atoms.

Preferred substituents of phenyl radicals $R_1$ or $R_2$ are e.g. 1 or 2 alkyl groups each containing 1 to 4 carbon atoms, alkoxy groups containing 1 to 4 carbon atoms, and chlorine. Phenyl radicals $R_1$ or $R_2$ are preferably unsubstituted.

Preferred alkyl and alkenyl radicals $R_1$ and $R_2$ contain 1 to 4 and 3 or 4 carbon atoms respectively.

Interesting compounds falling within the scope of the formula (1) are those of the formula

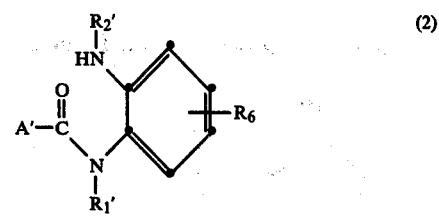
(2)

wherein A' is a radical of the formula

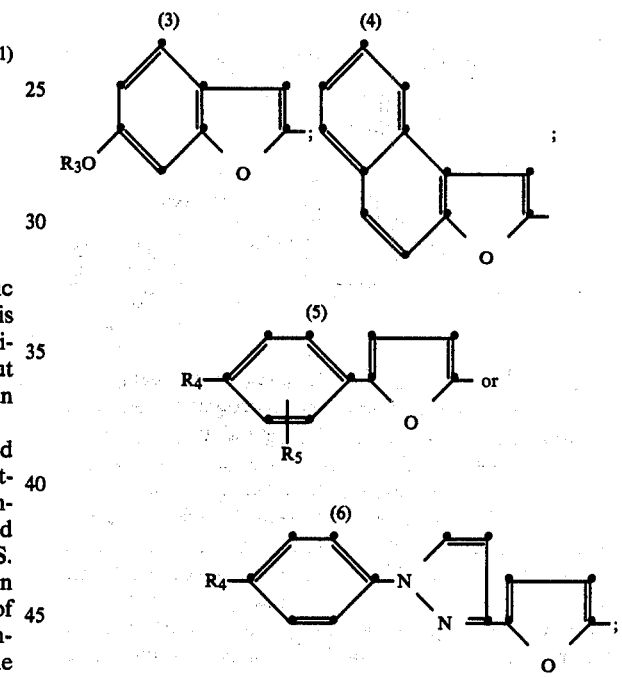

wherein $R_3$ is alkyl of 1 to 4 carbon atoms which is unsubstituted or substituted by phenyl or alkoxy of 1 to 4 carbon atoms or alkenyl of 3 or 4 carbon atoms, each of $R_4$ and $R_5$ independently is hydrogen, chlorine or methyl, each of $R_1'$ or $R_2'$ independently is alkyl of 1 to 4 carbon atoms, alkenyl of 3 or 4 carbon atoms, cyanoalkyl of 2 to 4 carbon atoms, carbamoylmethyl, alkoxycarbonylmethyl containing 1 to 3 carbon atoms in the alkoxy moiety, benzyl, hydroxyalkyl of 2 or 3 carbon atoms or phenyl, but only one of $R_1'$ and $R_2'$ can be phenyl, and $R_6$ is hydrogen, chlorine, alkyl of 1 to 4 carbon atoms, carboxamides, carboxylic acid esters, sulfonamides and sulfophenyl esters, trifluoromethyl, alkylsulfonyl of 1 to 4 carbon atoms or arylsulfonyl.

Particularly interesting N-acyl-o-phenylenediamines are those of the formula

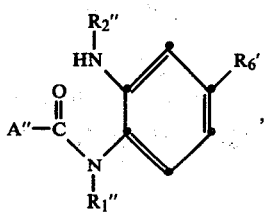

wherein A″ is a radical of the formula

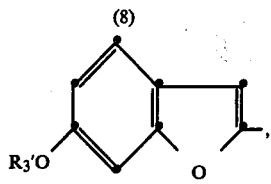

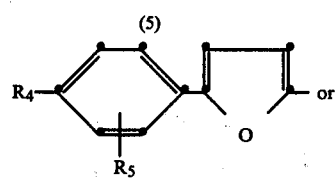

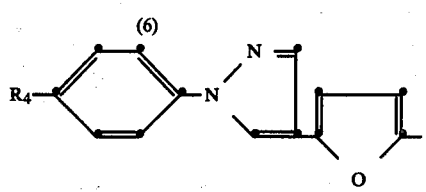

wherein $R_3'$ is alkyl of 1 to 4 carbon atoms and each of $R_4$ and $R_5$ independently is hydrogen, chlorine or methyl, each of $R_1''$ and $R_2''$ independently is alkyl of 1 to 4 carbon atoms, alkenyl of 3 or 4 carbon atoms, cyanoalkyl of 2 or 3 carbon atoms, alkoxycarbonylmethyl containing 1 to 3 carbon atoms in the alkoxy moiety, benzyl or phenyl, but only one of $R_1''$ and $R_2''$ can be phenyl, and $R_6'$ is hydrogen, methyl, chlorine, alkylsulfonyl of 1 to 4 carbon atoms, phenylsulfonyl, cyano, trifluoromethyl, phenoxysulfonyl, alkoxycarbonyl containing a total of 2 to 5 carbon atoms or $CONY_1Y_2$ or $SO_2NY_1Y_2$, wherein $Y_1$ is hydrogen, alkyl of 1 to 4 carbon atoms, alkenyl of 3 or 4 carbon atoms, hydroxyalkyl of 2 to 4 carbon atoms, alkoxyalkyl containing a total of 3 to 6 carbon atoms, cyclohexyl or benzyl, and $Y_2$ is hydrogen, alkyl of 1 to 4 carbon atoms, or $Y_1$ and $Y_2$ together with the nitrogen atom to which they are attached can also form a morpholine ring. $R_1''$ and $R_2''$ are preferably alkyl of 1 to 4 carbon atoms or benzyl.

Preferred compounds are
(a) N-acyl-o-phenylenediamines of the formula

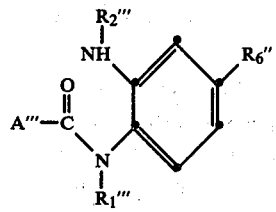

wherein A‴ is a radical of the formula

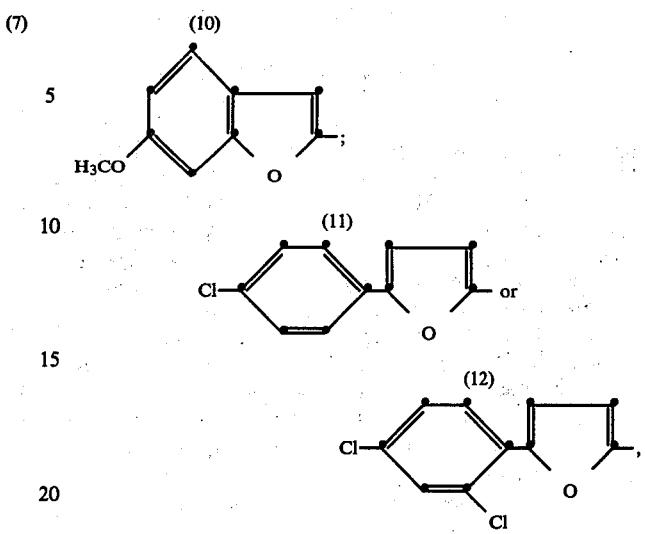

$R_1'''$ is alkyl of 1 to 4 carbon atoms, phenyl or benzyl, $R_2'''$ is alkyl of 1 to 4 carbon atoms, cyanoalkyl of 2 or 3 carbon atoms or alkoxycarbonylmethyl containing 1 to 3 carbon atoms in the alkoxy moiety, and $R_6''$ is hydrogen, alkylsulfonyl of 1 to 4 carbon atoms, phenoxysulfonyl, sulfamoyl, alkylsulfamoyl of 1 to 4 carbon atoms, alkoxycarbonyl containing 1 to 3 carbon atoms in the alkoxy moiety, or cyano; and, in particular, (b) N-acyl-o-phenylenediamines of the formula

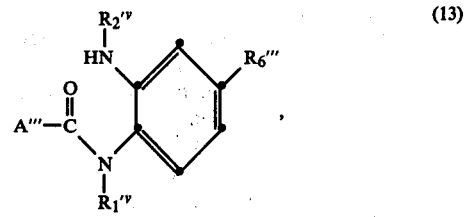

wherein A‴ is as defined above and $R_1'^v$ is methyl or benzyl, $R_2'^v$ is methyl or phenyl and $R_6'''$ is hydrogen, methylsulfonyl, methylsulfamoyl or phenoxysulfonyl.

Preferred compounds are those of the formulae (2), (7), (9) and (13), wherein A′, A″ and A‴ correspond to the radicals of the formulae (3), (5), (8), (10) and (11).

N-Acyl-o-phenylenediamines of the formulae (1), (2), (7), (9) and (13) can be obtained by different methods. Thus compounds of the formula (1) can be obtained by treating a benzimidazolium compound of the formula

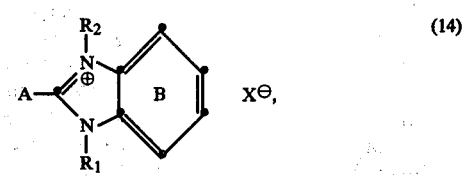

wherein A, B, $R_1$ and $R_2$ have the given meanings, and $X^⊕$ is a colourless anion which is equivalent to the fluorescent whitener cation, with a base.

The treatment is carried out at a pH value of at least 8 and in the temperature range between 0° and 120° C. The cleavage of the benzimidazolium ring by hydrolysis proceeds in accordance with the reaction scheme:

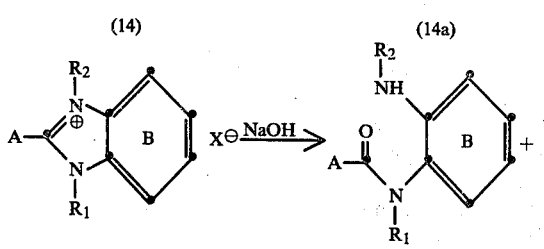

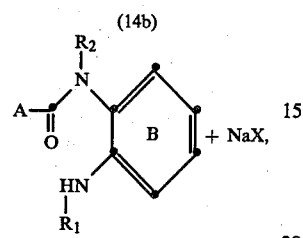

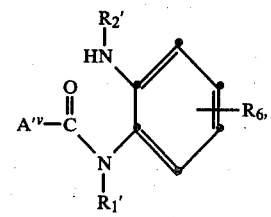

wherein $A'^v$ is a radical of the formula

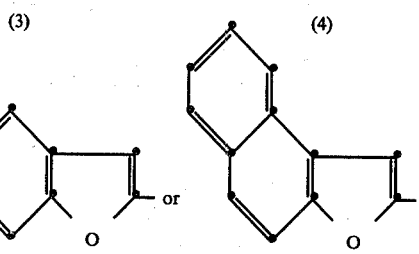

wherein A, B, $R_1$, $R_2$ and $X^\oplus$ have the given meanings. The two isomers of the formulae (14a) and (14b) can be formed during the ring cleavage if $R_1$ is different from $R_2$ or if the structure of the molecule is asymmetric because of substitution at the ring B.

Examples of suitable bases are: hydroxides of alkali metals and alkaline earth metals, aqueous amines or ammonium hydroxides, such as ammonia. Salts of strong bases with weak acids, such as potassium carbonate, can also be employed under reaction conditions in which the salts initially formed are unstable and decompose on hydrolysis, e.g. at elevated temperature.

The preferred base is aqueous sodium or potassium hydroxide. The amount of base depends on its pH value, which is the criterion for a complete reaction. It is advantageous to employ sufficient equivalents of base per mole of compound of the formula (14) such that the pH value of the reaction solution is at least 8. In general, at least one equivalent of base and preferably a small excess of 1 to 10% of a strong base is employed. In certain cases a larger excess of strong base is necessary to obtain a complete opening of the imidazole ring. The reaction is advantageously carried out in aqueous medium at a temperature at which the starting material is still soluble, preferably in the temperature range between 60° and 100° C. Organic solvents can be added to the reaction mixture if the starting materials are insufficiently soluble or if the reaction has to be carried out at low temperature owing to the presence of substituents which are susceptible to hydrolysis, e.g. a carboxylic acid ester group. In principle, all inert organic solvents are suitable, especially those which are completely or partially miscible with water, such as alcohols (methanol, ethanol, isopropanol, n-propanol, butanol, ethylene glycol), ethers (dioxane, ethylene glycol monomethyl ether), ketones (acetone, methyl ethyl ketone, methyl isobutyl ketone), sulfoxides (dimethyl sulfoxide) or amines (pyridine, triethylamine).

The final products can be isolated from the reaction mixture by conventional methods which are known per se. In practice, it is advantageous to carry out the reaction in an aqueous solution from which the usually reluctantly soluble reaction product of the formula (1) precipitates and can be easily collected by filtration. By washing it with water, the reaction product is obtained free of ions.

Compounds of the formula in which $R_3$ is alkyl of 1 to 4 carbon atoms which is unsubstituted or substituted by phenyl or alkoxy of 1 to 4 carbon atoms or alkenyl of 3 or 4 carbon atoms, each of $R_1'$ and $R_2'$ independently is alkyl of 1 to 4 carbon atoms, alkenyl of 3 or 4 carbon atoms, cyanoalkyl of 2 to 4 carbon atoms, carbamoylmethyl, alkoxycarbonylmethyl containing 1 to 3 carbon atoms in the alkoxy moiety, benzyl or hydroxyalkyl of 2 to 3 carbon atoms, and one of $R_1'$ and $R_2'$ is also phenyl, and $R_6$ is hydrogen, chlorine, alkyl of 1 to 4 carbon atoms, carboxamides, carboxylic acid esters, sulfonamides and sulfophenyl esters, cyano, trifluoromethyl, alkylsulfonyl of 1 to 4 carbon atoms or arylsulfonyl, can also be obtained by condensing an aldehyde of the formula

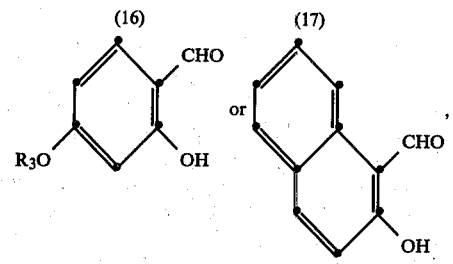

wherein $R_3$ is as defined above, with a 2-chloromethylbenzimidazolium salt of the formula

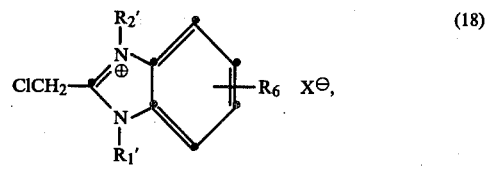

wherein $R_1'$, $R_2'$ and $R_6$ have the above meanings and $X^\oplus$ is a colourless anion which is equivalent to the benzimidazolium cation, in the presence of a base.

Suitable bases for the above reaction are: hydroxides, oxides, carbonates and alcoholates of alkali metals and alkaline earth metals, such as sodium hydroxide, magnesium oxide, sodium methylate and, in particular, potassium or sodium carbonate. The amount of base employed is between the equivalent amount, i.e. 2 equivalents per equivalent of compound of the formula (18), and a multiple excess. An excess is employed in particular whenever at elevated temperature a portion of the base is consumed by reaction with the solvent, for example when using sodium hydroxide in dimethyl formamide.

The reaction temperature depends on the compound to be condensed and the condensation agent within wide limits. It is preferably between 60° and 150° C. Many organic solvents are suitable for use as reaction medium, especially strongly polar compounds, such as dimethyl formamide, N-methylpyrrolidone, tetramethyl urea, pyridine or acetonitrile.

The starting compounds of the formula (18) are obtained e.g. by condensation of chloroacetic acid with correspondingly substituted o-phenylenediamines of the formula

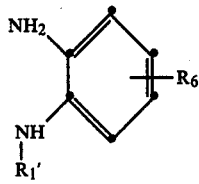

and subsequent quaternisation with alkylating agents of the formula $R_2'X$, wherein $R_1'$, $R_2'$ and $R_6$ have the given meanings.

The benzimidazolium compounds of the formula

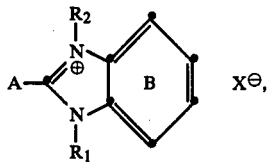

(14)

wherein A is a colourless carbocyclic or heterocyclic aromatic radical, each of $R_1$ and $R_2$ independently is an alkyl, alkenyl or phenyl radical which is unsubstituted or substituted by non-chromophoric groups, but only one of $R_1$ and $R_2$ can be phenyl, and $X^\ominus$ is a colourless anion which is equivalent to the fluorescent whitener cation and the ring B can also be substituted by non-chromophoric groups, are obtained by reacting a N-acyl-o-phenylenediamine of the formula

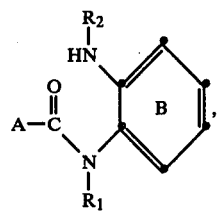

(1)

wherein A, B, $R_1$ and $R_2$ have the above meanings, with an acid HX.

Suitable acids HX are those organic or inorganic acids which, in accordance with their valency, are able to form a monovalent or polyvalent salt. Preferred acids are those which are able to form salts of high water-solubility, e.g. aliphatic monocarboxylic acids containing 1 to 6 carbon atoms which can be substituted by 1 to 5 hydroxyl groups or a ketone group, unsaturated aliphatic carboxylic acids containing 3 to 6 carbon atoms, dicarboxylic and tricarboxylic acids containing 2 to 6 carbon atoms which can be additionally substituted by 1 to 4 hydroxyl groups or simply unsaturated, or alkanephosphonic acids and their monoalkyl esters or mono- or dialkyl esters or mono- or dialkenyl esters of phosphorous acid, each containing a total of 1 to 6 carbon atoms, and mixtures thereof.

Particularly preferred acids are formic acid, acetic acid, propionic acid, glycolic acid, lactic acid, acrylic acid, methanephosphonic acid, dimethyl phosphite and diethyl phosphite.

The conversion of the compounds of the formula (1) into those of the formula (14) is effected in simple manner by stirring N-acyl-o-phenylenediamines of the formula (1) with the desired acid in a suitable inert solvent in the temperature range from 0° to 120° C. To hasten the reaction it is possible to employ a wetting agent which acts as solubiliser for the starting material. Water is preferably employed as solvent, but organic solvents can also be added if necessary, especially those which are miscible with water. Strong acids in high concentration react even at low temperature, whilst the reaction has to be carried out at elevated temperature, e.g. reflux temperature, if weak acids are employed, especially in low concentration.

Mixtures of isomers of the formulae (14a) and (14b) again yield homogeneous products in this cyclisation reaction.

The isolation of the resultant salts depends on their solubility.

If aqueous acids which yield sparingly soluble salts are employed, these latter crystallise out on cooling. In many cases, however, crystallisation is not desirable (e.g. for producing aqueous formulations), for which reason acids of readily soluble salts are deliberately employed. In this case it is advantageous to use at least aquivalent amounts of acid, while to obtain a virtually neutral solution the acid can be employed in up to about 30% excess. If the pH value is of no consequence, then the acid can be employed in substantial excess (up to ten-fold).

The manufacture of benzimidazolium compounds of the formula (14) from N-acyl-o-phenylenediamines of the formula (1), which in turn are obtained from benzimidazolium compounds of the formula (14), affords the particular advantage of making it possible, in simple manner, to exchange the anion of a benzimidazolium compound of the formula (14) in very good yield for any other anion. By means of this procedure it is possible to convert the reluctantly water-soluble methosulfates, chlorides or bromides obtained in the production of benzimidazolium fluorescent whiteners, in simple manner, into substantially more readily water-soluble salts of lower carboxylic acids and phosphonic acids or phosphorous acid esters, the benzimidazolium fluorescent whitener being optionally obtained in the form of a highly concentrated stable aqueous solution of the corresponding novel salt.

Cationic fluorescent whitening agents in solid form possess a number of negative properties. Attempts have therefore already been made to eliminate these drawbacks by preparing aqueous or organic, in particular concentrated, solutions. Such liquid formulations are also necessary in particular for whitening polyacrylonitrile fibres in the gel state. In this method of whitening, depending on the dyeing unit and metering device, relatively concentrated solutions of fluorescent whitener are used. For this reason, particular importance attaches to the solubility of the fluorescent whiteners and the stability of the fluorescent whitener solutions. The limits of the requirements made of the solubility are determined by the nature of the dyeing unit and of the pick-up resulting therefrom, by the form of the subsequent addition of fluorescent whitening agent, and also by the dyeing temperature. It may be generally stated that only readily soluble products ensure an adequate operating safety and accordingly are suitable for this application. The fact is that fluorescent whitener solutions make possible a higher yield and thus a more rapid exhaustion onto the fibre.

As normally a very substantial amount of fluorescent whitening agent must be dissolved per batch, there exists in the trade a desire for liquid formulations because of easier handling, volumetric addition, elimination of dust, and the formation of lumps as a result of caking.

Swiss patent specification No. 590 965 describes the manufacture of solutions of cationic fluorescent whitening agents which are completely miscible with water. These solutions, however, contain a high proportion of assistants, such as urea and other polar organic compounds which are not consumed during the application and which pollute the wastewater. They are therefore undesirable for economic and ecological reasons. They also have the drawback that they are often not stable or only have low concentrations of fluorescent whitener.

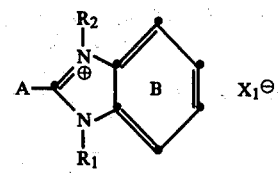

wherein A a colourless, carbocyclic or heterocyclic aromatic radical, each of $R_1$ and $R_2$ independently is an unsubstituted or substituted alkyl, alkenyl or phenyl radical, but only one of $R_1$ and $R_2$ can be phenyl, and $X_1^\ominus$ is the formiate, acetate, propionate, glycolate, lactate, acrylate, methanephosphonate or dimethyl or diethyl phosphite anion, or mixtures thereof, and the ring B can also be substituted by non-chromophoric groups, (b) 0 to 14% by weight of the acid corresponding to the anion $X^\ominus$ and (c) water to bulk the formulation to 100%.

The solutions of the invention contain preferably 5 to 40%, in particular 10 to 35%, of benzimidazolium fluorescent whitening agent, and preferably 0.1 to 35% of the acid corresponding to the anion $X^\ominus$.

Preferred acids are formic, acetic, propionic, glycolic, lactic, acrylic and methanephosphonic acid, as well as dimethyl and diethyl phosphite. Preferred benzimidazolium fluorescent whitening agents are those of the formulae

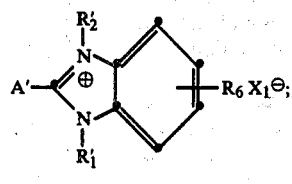 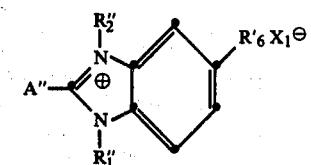

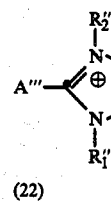 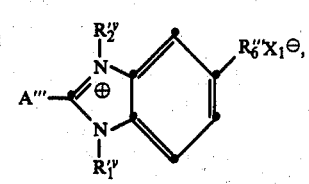

wherein A', A'', A''', $R_1'$, $R_1''$, $R_1'''$, $R_1''''$, $R_2'$, $R_2''$, $R_2'''$, $R_2''''$, $R_6$, $R_6'$, $R_6''$, $R_6'''$ and $X_1^\oplus$ have the meanings given above.

Preferred compounds of the formulae (20), (21), (22) and (23) are those wherein A', A'' and A''' are radicals of the formula (3), (8) or (10).

The solutions of this invention are especially suitable for whitening polyacrylonitrile fibres in the gel state. They are chemically and physically stable over prolonged periods of time when stored under the fluctuating temperature conditions which occur, i.e. the solid product neither decomposes nor precipitates, not even when diluted with water in any ratio. Salts dried by evaporation continue to remain water-soluble.

It has also been found that the virtually non-fluorescent N-acyl-o-phenylenediamines of the formula (1), and especially those wherein the radical A is a radical of the formula (3), (8) or (10), can be used as fluorescent whitening agents for treating man-made organic material. They are able to whiten in particular polyacryloni- In contradistinction thereto, the process described above makes it possible to obtain stable, concentrated aqueous solutions of low viscosity which are virtually free from any kind of organic additives or salts and are miscible with water in any ratio, without the occurrence of crystallisation.

As polyacrylonitrile is normally whitened in acid solution, e.g. in the presence of formic acid, the fluorescent whitener solution can contain, in addition to water, acid which is added in the desired excess, advantageously during the manufacture of the solution.

The stable, concentrated aqueous solutions of benzimidazolium fluorescent whitening agents of the present invention consist of (a) 0.1 to 40% by weight of at least one water-soluble benzimidazolium fluorescent whitening agent of the formula trile and copolymers thereof under the customary treatment conditions, i.e. in an acid dyebath and at elevated temperature, in virtually the same manner as the corresponding cationic compounds of the formula (14). Acid-modified polyester is often also whitened in a neutral treatment bath.

The above defined novel N-acyl-o-phenylenediamines and the stable aqueous fluorescent whitener solutions obtained therefrom can be used for whitening the most diverse man-made, regenerated man-made or natural organic material or substances which contain such material.

Without any restriction being implied by the following classification, examples of organic materials which can be treated with fluorescent whitening agents are:

I. Man-made material of high molecular weight:

(a) polymerisation products based on organic compounds containing at least one polymerisable carbon-carbon double bond, that is to say their homopolymers of copolymers as well as their aftertreatment products, for example, crosslinking, grafting or degradation products, polymer blends, or products obtained by modification of reactive groups, for example polymers based on $\alpha,\beta$-unsaturated carboxylic acids or derivatives of such carboxylic acids, especially on acrylic compounds, for example acrylates, acrylic acid, acrylonitrile, acrylamides and their methacrylic analogues, on olefin hydrocarbons (for example ethylene, propylene, styrenes or dienes and also ABS polymers), and polymers based on vinyl and vinylidene compounds (for example vinyl chloride, vinyl alcohol and vinylidene chloride);

(b) polymerisation products which can be obtained by ring opening, for example, polyamides of the polycaprolactam type, and also polymers which are obtained both by polyaddition and by polycondensation, for example polyethers or polyacetals;

(c) polycondensation products or precondensates based on bifunctional or polyfunctional compounds with condensable groups, their homocondensation and co-condensation products, and aftertreatment products, for example polyesters, especially saturated polyesters (for example ethylene glycol, terephthalic acid polyester) or unsaturated polyesters (for example maleic acid-dialcohol polycondensates as well as their crosslinking products with copolymerisable vinyl monomers), unbranched and branched polyesters (also including those based on polyhydric alcohols, for example alkyd resins), polyamides (for example hexamethylenediamine adipate), maleic resins, melamine resins, their precondensates and analogues, polycarbonates and silicones;

(d) polyadducts, such as polyurethanes (crosslinked and uncrosslinked) and epoxide resins.

II. Regenerated man-made organic material, for example, cellulose esters of varying degrees of esterification (so-called 2½ -acetate or triacetate) or cellulose ethers, regenerated cellulose (viscose or cuprammonium cellulose), or their aftertreatment products, and casein plastics.

III. Natural organic material of animal or vegetable origin, for example based on cellulose or proteins, such as cotton, wool, linen, silk, natural film-forming resins, starch and casein.

The organic material to be whitened can be in the most diverse states of processing (raw materials, semifinished goods or finished goods). On the other hand, it can be in the form of structures of the most diverse shapes, for example predominantly three-dimensional structures such as sheets, profiles, injection mouldings, various machined articles, chips, granules or foams, and also predominantly two-dimensional structures, such as films, sheets, lacquers, coatings and impregnations or predominantly one dimensional bodies, such as filaments, fibres, flocks and wires. The above materials can, on the other hand, also be in an unshaped state, in the most diverse homogenous or inhomogenous forms of division, as for example in the form of powders, solutions, emulsions, dispersions, latices, pastes or waxes.

Fibrous material can be, for example, in the form of endless filaments (stretched or unstretched), staple fibres, flocks, hanks, textile filament yarns, threads, nonwovens, felts, waddings, flocked structures or woven textile or bonded textile fabrics, knitted fabrics, and papers, cardboards or paper pulps.

The compounds to be used according to the invention are of importance, inter alia, for the treatment of organic textile material, especially woven textile fabrics. If fibres which can be in the form of staple fibres or endless filaments or in the form of hanks, woven fabrics, knitted fabrics, fleeces, flocked substrates or bonded fabrics, are to be whitened according to the invention, this is advantageously effected in an aqueous medium, wherein the compounds in question are present in a finely divided form (suspensions, so-called microdispersions, or optionally solutions). If desired, dispersing agents, stabilisers, wetting agents and further assistants can be added during the treatment.

Depending on the type of whitening agent used, it can be advantageous to carry out the treatment in a neutral or alkaline or acid bath. The treatment is usually carried out in the temperature range from 20° to 140° C., for example at the boiling point of the bath or near it (about 90° C.).

Solutions or emulsions in organic solvents can also be used for the finishing according to the invention of textile substrates, as is practised in the dyeing industry in so-called solvent dyeing (pad-thermofixation application, or exhaust dyeing methods in dyeing machines).

The fluorescent whitening agents of the present invention can further be added to, or incorporated in, the materials before or during their shaping. Thus they can for example be added to the compression moulding composition or injection moulding composition during the manufacture of films and sheets (for example incorporation in polyvinyl chloride in a roll mill at elevated temperature) or of mouldings.

The fluorescent whitening agents of the present invention can, for example, also be employed in the following formulations:

(a) in mixtures with dyes (shading) or pigments (coloured pigments or especially, for example, white pigments), or as an additive to dyebaths, printing pastes, discharge pastes or reserve pastes, or for the aftertreatment of dyeing, prints or discharge prints;

(b) in mixtures with carriers, wetting agents, plasticisers, swelling agents, antioxidants, ultraviolet absorbers, heat stabilisers and chemical bleaching agents (chlorite bleach or bleaching bath additives);

(c) in admixture with crosslinking agents or finishing agents (for example starch or synthetic finishes), and in combination with a wide variety of textile finishing processes, expecially synthetic resin finishes (for example creaseproof finishes such as wash-and-wear, permanent-press or non-iron), as well as flameproof finishes, soft handle finishes, antisoiling finishes or antistatic finishes, or antimicrobial finishes;

(d) incorporation of the fluorescent whitening agents in polymeric carriers (polymerisation, polycondensation or polyaddition products, in a dissolved or dispersed form, for use, for example, in coating agents, impregnating agents or binders (solutions, dispersions and emulsions) for textiles, nonwovens, papers and leather;

(e) as additives to masterbatches;

(f) as additives to a wide variety of industrial products in order to render these more marketable (for example improving the appearance of soaps, detergents, pigments);

(g) in combination with other substances with fluorescent whitening properties;

(h) in spinning bath preparations, that is to say as additives to spinning baths which are used for improving the slip for the further processing of synthetic fibres, or from a special bath before the streching of the fibre;

(i) as scintillators for various purposes of a photographic nature, for example for electrophotographic reproduction or supersensitising;

(j) depending on the substitution, as laser dyes.

If the whitening process is combined with textile treatment or finishing methods, the combined treatment can in many cases advantageously be carried out with the aid of appropriate stable preparations which contain the fluorescent whitener compounds in a concentration such that the desired white effect is achieved.

In certain cases, the fluorescent whitening agents are made fully effective by an aftertreatment. This can be, for example, a chemical treatment (for example acid treatment), a thermal treatment or a combined chemical/thermal treatment. Thus, for example, the appropriate procedure to follow in whitening a number of fibre substrates, for example polyester fibres, with the fluorescent whitening agents of the present invention, is to impregnate these fibres with the aqueous dispersions (or optionally also solutions) of the whitening agents at temperatures below 75° C., for example at room temperature, and to subject them to a dry heat treatment at temperatures above 100° C., it being generally advisable additionally to dry the fibrous material beforehand at a moderately elevated temperature, for example at not less than 60° C. to about 130° C. The heat treatment in the dry state is then advantageously carried out at a temperature between 120° and 225° C., for example by heating in a drying chamber, by ironing within the specified temperature range or by treatment with dry, superheated steam. The drying and dry heat treatment can also be carried out in immediate succession or be combined in a single process stage.

The amount of fluorescent whitening agent of the present invention to be used, based on the weight of the material to be whitened, can vary within wide limits. A marked and lasting effect can be obtained even with very insignificant amounts, in certain cases 0.0001 percent by weight. But it is also possible to use amounts of up to 0.8 percent by weight and on occasion, up to 2 percent by weight. For most practical purposes, it is preferable to use amounts between 0.005 and 0.5 percent by weight.

For various reasons it is often advantageous not to use the fluorescent whitening agents by themselves, i.e. pure, but in admixture with a wide variety of assistants and extenders, for example anhydrous sodium sulfate, sodium sulfate decahydrate, sodium chloride, sodium carbonate, alkali metal phosphates, such as sodium or potassium orthophosphate, sodium or potassium pyrophosphate and sodium or potassium tripolyphosphates or alkali metal silicates.

The invention is illustrated by the following Examples, in which percentages are by weight. Unless otherwise indicated, melting and boiling points are uncorrected and usually unsharp.

EXAMPLE 1

48.3 g of the benzimidazolium compound of the formula

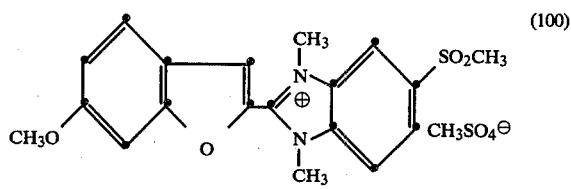

(100)

are dissolved at elevated temperature in 300 ml of water. With stirring, 13.4 g of 30% sodium hydroxide are added dropwise at 70° C. to the resultant solution such that the pH value is constantly between 10 and 11, whereupon a dense white precipitate of the reaction product forms. The suspension is cooled to room temperature, filtered with suction, and the residue is washed neutral with water and dried in vacuo at 100° C., affording 36.8 g (95% of theory) of the compound of the formula

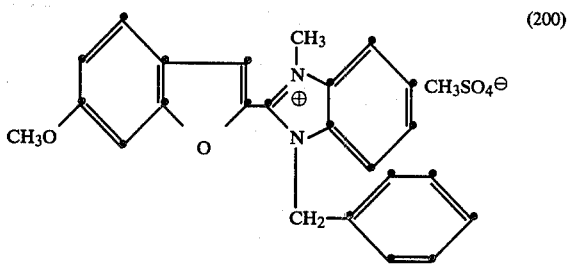

(200)

with a melting point of 183°–184° C. The compound can be recrystallised from n-propanol/water (7:3).

EXAMPLE 2

With stirring, 6.7 g of 30% sodium hydroxide are added dropwise at 70° C. to a solution of 24.0 g of the benzimidazolium compound of the formula

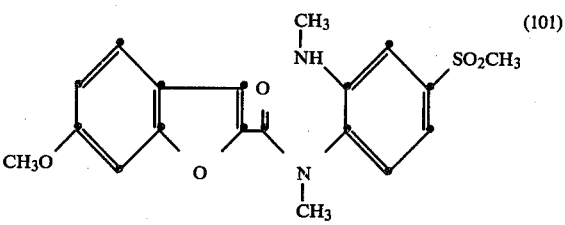

(101)

in 150 ml of water such that the pH value does not rise above 10.5. The mixture is cooled to room temperature, a further 6.7 g of 30% sodium hydroxide being added at about 60° C. After the initially resinous precipitate has decomposed, it is collected with suction, washed neutral with water and dried in vacuo at 60° C., affording 18.4 g (95% of theory) of a mixture of isomers of the formulae

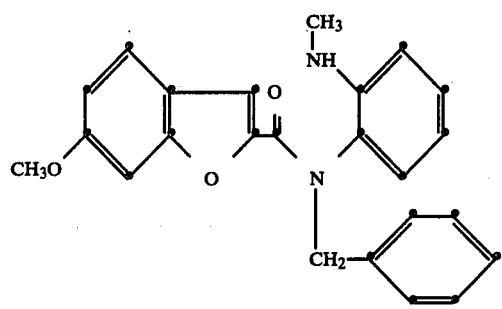
(201a)

and

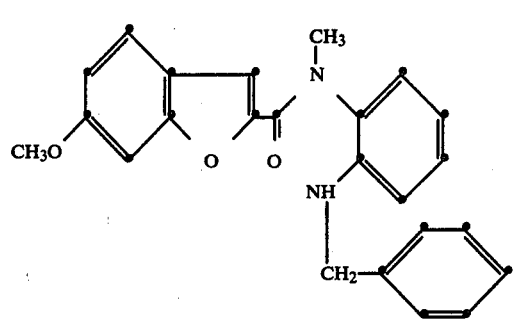
(201b)

which melts at about 60°–120° C. The mixture consists principally of the more readily soluble form (201a). Recrystallisation from isopropanol yields the other isomer (201b) with a melting point of 166° C.

EXAMPLE 3

5.0 g of the benzimidazolium compound of the formula

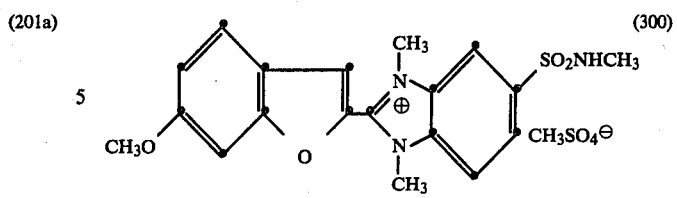
(300)

are treated at 95° C. with 5.1 ml of 2N sodium hydroxide in 15 ml of water in accordance with Example 1. Yield: 3.9 g of the compound of the formula

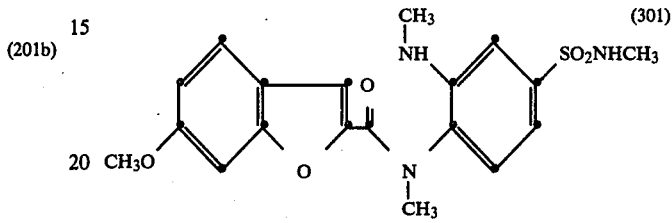
(301)

with a melting point of 179° C. after recrystallisation from n-propanol/water (8:2).

The compounds of the formulae (302) to (304), and/or their isomers, are obtained in analogous manner from the corresponding benzimidazolium methosulfates:

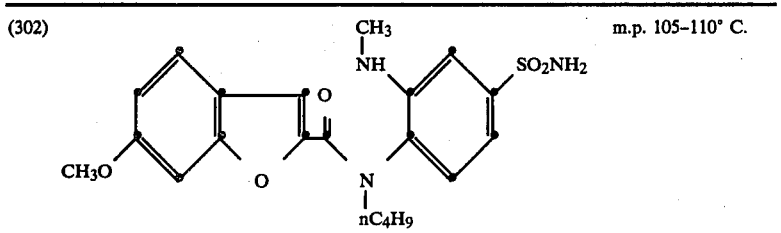
(302) m.p. 105–110° C.

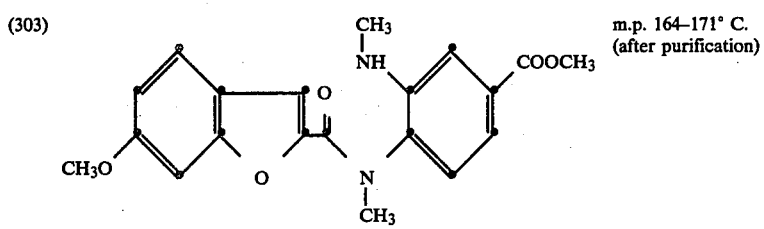
(303) m.p. 164–171° C. (after purification)

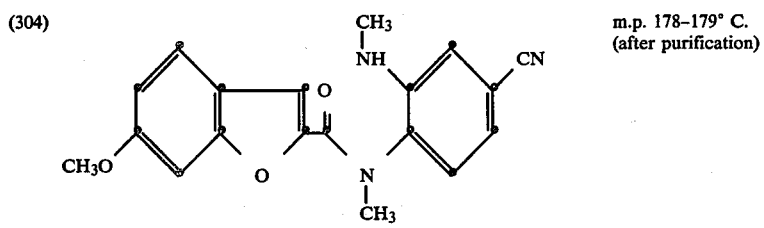
(304) m.p. 178–179° C. (after purification)

The compound of the formula (303) is purified by stirring the crude product (3.4 g) at room temperature in 50 ml of methylene chloride, filtering the suspension, concentrating the filtrate to dryness and recrystallising the residue from isopropanol. The compound of the formula (304) (3.2 g) is treated in the same manner and recrystallised from n-propanol/water (4:1).

EXAMPLE 4

In a manner similar to that described in Examples 1, 2 and 3, the compounds of the formulae (405) to (409) and their isomers (see Table 1) are obtained from the benzimidazolium salts of the formulae (400) to (402) [X=CH₃SO₄], (403) [X=Cl] and (404) [X=Br].

TABLE 1

| Compound | R₁ | R₂ | R₃ | R₄ | R₅ | Compound | Melting point after recrystallisation from |
|---|---|---|---|---|---|---|---|
| (400) | CH₃ | CH₃ | SO₂CH₃ | Cl | H | (405) | 216° C. ethyleneglycol monomethyl ether |
| (401) | CH₃ | CH₃ | SO₂OC₆H₅ | Cl | H | (406) | 154° C. n-propanol |
| (402) | CH₃ | C₆H₅ | H | Cl | Cl | (407) | 164° C. n-butanol |
| (403) | CH₃ | CH₂CN | SO₂CH₃ | Cl | H | (408) | 168–186° C. (decomp.) n-propanol |
| (404) | CH₃ | CH₂COOC₂H₅ | SO₂NHCH₃ | Cl | H | (409) | 80–89° C. (decomp.) isopropanol |

The compound of the formula (408) in admixture with its isomers can be obtained as follows: With stirring, 10 ml of 1N sodium hydroxide are added dropwise at 50° C. to a solution of 4.6 g of the compound of the formula (403) in 230 ml of methanol and 180 ml of water. After cooling to room temperature, the methanol is removed in vacuo. The precipitated product is collected with suction, washed with water and dried in vacuo, affording 3.9 g of crude product which is purified in the same manner as compound (303) in Example 3 by extraction with methylene chloride and crystallisation from methylene chloride/n-propanol.

The compound of the formula (409) and/or its isomers can be obtained as follows: With stirring, a solution of 0.2 g of sodium hydroxide in 10 ml of ethanol is added dropwise at room temperature to a solution of 2.8 g of the compound of the formula (404) in 100 ml of ethanol and 5 ml of dimethyl formamide. After 1 hour the solution is completely concentrated in vacuo at room temperature and the residue is stirred in 30 ml of ice-water at 0° to 5° C. The precipitated product is collected with suction, washed neutral with water and dried in vacuo over calcium chloride, affording 2.3 g of crude product which is purified in the same manner as compound (303) in Example 3 by extraction with methylene chloride and recrystallisation from isopropanol.

EXAMPLE 5

With stirring, a solution of 0.8 g of sodium hydroxide in 20 ml of ethanol is added dropwise at room temperature to a solution of 10.0 g of the compound of the formula wherein X is a mixture of chlorine and bromine, in 150 ml of ethanol. After 10 minutes the precipitated product is collected with suction, washed with 50% aqueous alcohol and dried in vacuo. The crude product is stirred at room temperature in 100 ml of methylene chloride and the insoluble portion is removed by filtration. The concentrated filtrate is crystallised twice from isopropanol, affording the compound of the formula

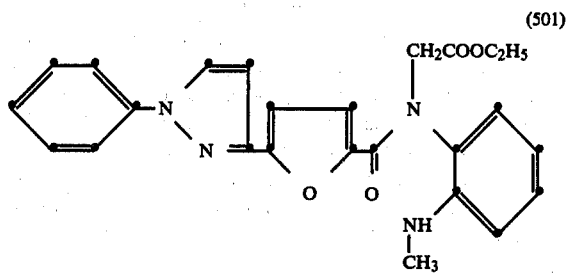

with a melting point of 157° (unsharp).

EXAMPLE 6

With stirring, 5.7 g of dimethyl sulfate are added dropwise at 100° C. to a solution of 13.0 g of the compound of the formula

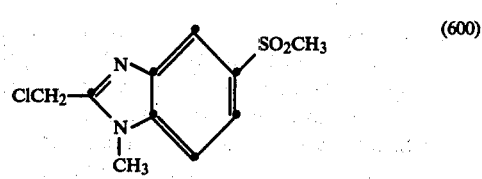

in 250 ml of chlorobenzene. Stirring is continued for a further 2 hours at this temperature, then the reaction mixture is cooled and the precipitate is collected with suction, washed with chlorobenzene and dried in vacuo at 100° C., affording 16.6 g (86% of theory) of the compound of the formula

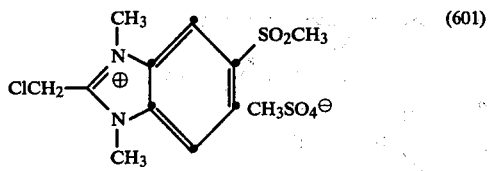
(601)

with a melting point of 185° C. (with decomp.). The compound can be recrystallised from methanol.

While introducing a weak flow of nitrogen, 7.7 g of the above product of the formula (601), 3.05 g of 2-hydroxy-4-methylbenzaldehyde and 8.3 g of anhydrous potassium carbonate are stirred at room temperature in 30 ml of dimethyl formamide. The suspension is heated in the course of half an hour to 90° C. and stirred for 1 hour at this temperature. By intensifying the flow of nitrogen, 15 ml of solvent are distilled off at 90° C. under normal pressure and the remainder is removed in vacuo. After addition of 70 ml of water the aqueous phase is decanted and the resinous residue is crystallised from 60 ml of isopropanol. The precipitate is collected with suction, washed repeatedly with isopropanol and water and dried at 100° C. in vacuo, affording 4.6 g of the compound of the formula (101) with a melting point of 182°–183° C. after recrystallisation from n-propanol/water (7:3).

The starting compound of the formula (600) is obtained by heating equivalent amounts of 2-aminomethyl-5-methylsulfonyl aniline with chloroacetyl chloride in glacial acetic acid for 3 hours at 80°–90° C. in the presence of sodium acetate. Melting point: 188°–189° C.

EXAMPLE 7

57.6 g of the product of the formula (101) [it is also possible to use the corresponding amount of moist filter cake] are suspended in 9.4 g of acetic acid and sufficient deionised water to give a total weight of 250 g. The suspension is stirred under weak reflux until complete solution is attained (about 2½ hours). The resultant yellowish stable aqueous solution of the acetate of the formula

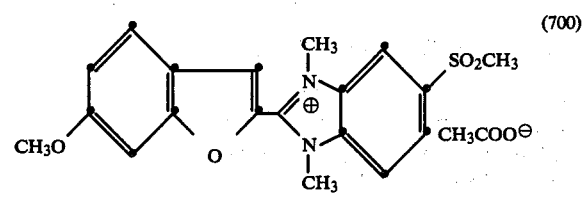
(700)

has a concentration of 28.6%, based on the fluorescent whitening agent of the formula (100), and a pH value of 5.3. It can be diluted with water in any desired ratio. A 15% aqueous solution is unchanged in appearance and concentration after storage for 3 months at 25 C. or 60° C. By comparison, the solubility of the methosulfate of the formula (100) is 0.5% at room temperature.

If hydrochloric acid or sulfuric acid is used in excess instead of acetic acid, the corresponding chloride (melting point 180°–240° C., depending on the content of water of crystallisation) or hydrogen sulfate (melting point 245°–247° C.) respectively, is obtained. Both crystallise on cooling.

By carrying out the procedure of this Example using the compound of the formula (301) instead of that of the formula (101), the compound of the formula (300) is obtained in the form of the acetate. The resultant acetate solution, which is diluted with water to a concentration of 18%, based on the fluorescent whitening agent of the formula (300), has a pH value of 5.4 and is stable when stored.

EXAMPLE 8

1 part of the compound of the formula (101) is heated with 1 part of one of the acids listed below in 1.3 parts of water and the mixture is diluted with water to 4 parts, affording the corresponding salts in solution. The salts are partially stable on cooling and when stored.

| Acid | Salt |
|---|---|
| succinic acid | crystallises |
| oxalic acid | crystallises |
| malonic acid | crystallises |
| maleic acid | oily |
| fumaric acid | crystallises |
| glycolic acid | solution |
| malic acid | crystallises |
| tartaric acid | crystallises |
| lactic acid | solution |
| citric acid | crystallises |
| formic acid | solution |
| methanephosphonic acid | solution |
| propionic acid | solution |
| acrylic acid | solution |
| glyoxylic acid monohydrate | crystallises |
| dimethyl phosphite | solution |
| diethyl phosphite | solution |

Stable solutions of the corresponding acetates are obtained by reacting the compound of the formula (301) or (302) in analogous manner with aqueous acetic acid. The compound of the formula (407) is likewise converted with acetic acid into the acetate of the formula (402), wherein X is $CH_3COO$. This acetate remains in solution at room temperature.

1 part of the compound of the formula (405) is dissolved under reflux in 0.5 part of formic acid and 0.5 part of lactic acid and 1.3 parts of water. The solution is stable at room temperature.

1 part of the compound of the formula (406) is dissolved under reflux in 1 part of a 1:1:1 mixture of acetic acid/propionic acid/lactic acid and 1.3 parts of water. No precipitation occurs after cooling to room temperature.

Table 2 lists a number of further N-acyl-o-phenylenediamine derivatives (the isomeric forms are also partially formed) which can be obtained according to Examples 1 to 5 and which are converted into the corresponding benzimidazolium salts in accordance with Example 8, formula (101), with an acid HX, i.e. formic acid, acetic acid, propionic acid, glycolic acid, lactic acid, acrylic acid, dimethyl phosphite, diethyl phosphite or methanephosphonic acid, where X forms the anion of these acids.

TABLE 2
| Compound | N—Acyl-o-phenylenediamine | Benzimidazolium salt |
|---|---|---|
| (800) | 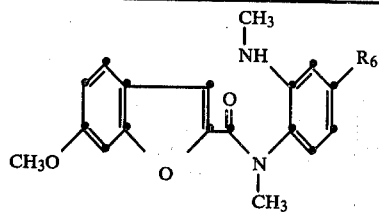 | 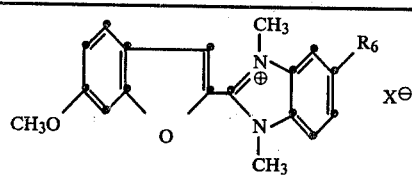 |
$R_6 = -SO_2NH_2, -SO_2NHCH_2CH_2OCH_3, -SO_2N(CH_3)_2, -SO_2N\underset{\phantom{x}}{\bigcirc}O, -SO_2NHCH_2CH_2OH, -COOC_2H_5,$
$-CN, -CF_3, -SO_2C_6H_5, -SO_2NH-\underset{\phantom{x}}{\bigcirc}H$
| | | |
|---|---|---|
| (801) | 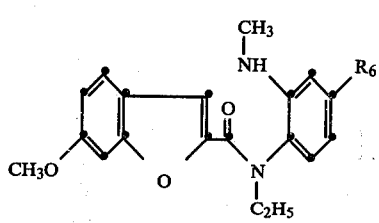 | 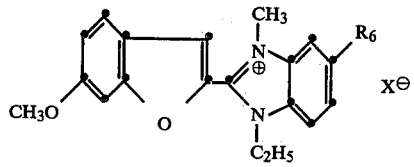 |
$R_6 = -SO_2NH_2, -SO_2NHC_2H_5$
| | | |
|---|---|---|
| (802) | 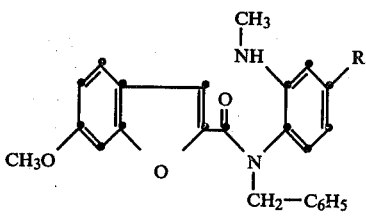 | 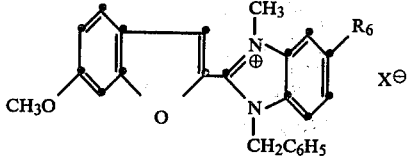 |
$R_6 = -SO_2NH_2, -SO_2NH-CH_2C_6H_5, -CONH_2, -CF_3, -Cl, -CH_3$
| | | |
|---|---|---|
| (803) | 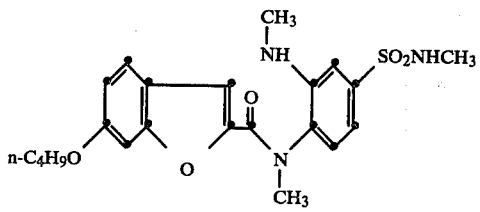 | 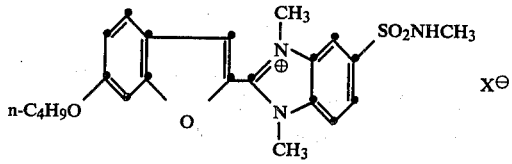 |
| (804) | 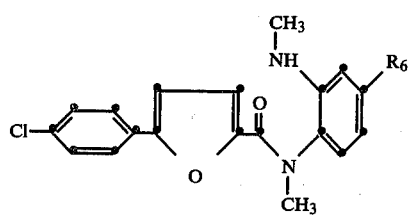 | 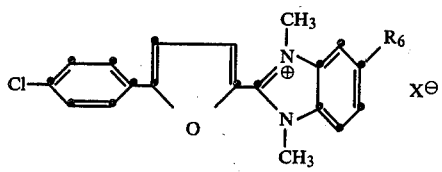 |
$R_6 = -CN, -SO_2C_6H_5$
| | | |
|---|---|---|
| (805) | 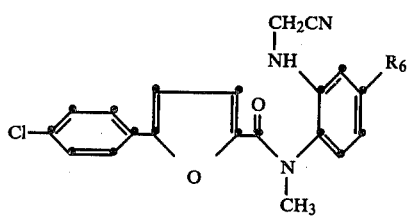 | 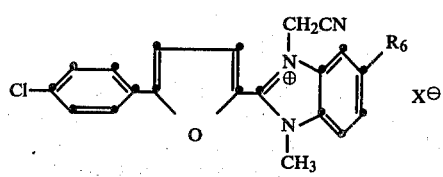 |

TABLE 2-continued

| Compound | N—Acyl-o-phenylenediamine | Benzimidazolium salt |
|---|---|---|

$R_6 = -SO_2NHCH_3, -SO_2NHCH_2CH_2OCH_3$ (806)

(807)

(808)

(809)

$R_4 = H, Cl$ (810)

(811)

EXAMPLE 9

7.7 g of the mixture of isomers of the formulae (201a) and (201b) are stirred for 4 hours under reflux in 1.5 g of acetic acid and 20 ml of deionised water until all is dissolved. The resultant yellowish, stable aqueous solution of the acetate of the formula (900)

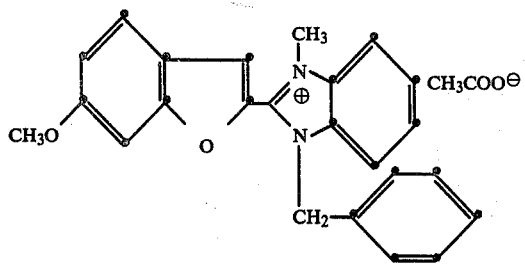

can be diluted with water in any ratio, has a pH value of 4.7 and an active substance concentration of 33%, based on the compound of the formula (200). By comparison, the solubility of the methosulfate of the formula (200) is 0.5% at room temperature.

EXAMPLE 10

0.3 g of the compound of the formula (101), (201a and 201b), (301), (403) or (408) is dissolved in 270 ml of softened water. To this solution are added 0.3 g of the adduct of 1 mole of stearyl alcohol with 35 moles of ethylene oxide, 0.3 g of the adduct of 1 mole of p-tert-octylphenol with 8 to 9 moles of ethylene oxide and 30 ml of 95% ethanol. Then 8 g of polyacrylonitrile staple fabric are padded with this solution to a pick-up of 90%. The padded fabric is then put at a liquor ratio of 1:25 into a warm bath of 50° C. which contains 1 g/l of 85% formic acid (pH value 2.5). The temperature is raised to 100° C. in the course of 10 minutes. This temperature is kept for 20 minutes, then the bath is cooled to 50° C. in the course of 5 minutes. The fabric is subsequently rinsed in softened water, centrifuged and dried with an iron at 160°–170° C. The treated fabric has a strong white effect.

A yarn with a strong white effect is obtained by using the same amount of a hank of modified polyacrylonitrile yarn (Courtelle ®, sold by Courtaulds, London) instead of the polyacrylonitrile staple fabric used in this Example, and drying at 140°–150° C.

EXAMPLE 11

0.3 g of the compound of the formula (101), (201a and b) or (301) is dissolved in 270 ml of softened water. To this solution are added 0.3 g of the adduct of 1 mole of stearyl alcohol with 35 moles of ethylene oxide, 0.3 g of the adduct of 1 mole of p-tert-octylphenol with 8 to 9 moles of ethylene oxide and 30 ml of 95% ethanol. Then 8 g of acid-modified polyester fabric are padded with this solution to a pickup of 65%. The padded fabric is then put in a liquor ratio of 1:25 into warm water of 50° C. The temperature is raised to 100° C. in the course of 10 minutes. This temperature is kept for 20 minutes, then the bath is cooled to 50° C. in the course of 5 minutes. The fabric is subsequently rinsed in softened water, centrifuged and dried with an iron at 180°–190° C. The treated fabric has a strong white effect.

EXAMPLE 12

Polyacrylonitrile fabric is put in the liquor ratio of 1:20 into an aqueous bath which contains, based on the weight of the fabric, 0.1% of the compound of the formula (700) and 1 g/l of an adduct of 30 to 35 moles of ethylene oxide with 1 mole of stearyl alcohol and 1.5 ml of 85% formic acid. The bath is then heated to 97° C. in the course of 30 minutes, kept at this temperature for 30 minutes, and then cooled to 40° C. in the course of 15 minutes. The fabric is rinsed in water and dried at 160° C. It has a strong white effect.

EXAMPLE 13

A rinsed, stretched, and undried polyacrylonitrile cable obtained by the sodium thiocyanate wet spinning process is immersed at 20° C. in the liquor ratio 1:10 for 30 seconds in an aqueous solution which contains 0.1 g/l of the compound of the formula (700) or (900), and 0.5 ml of 98% sulfuric acid (pH value of the solution: 2).

The cable is subsequently briefly rinsed in water and dried at 95° C. in the air. The treated polyacrylonitrile cable has a strong white effect.

What is claimed is:

1. A N-acyl-o-phenylenediamine of the formula

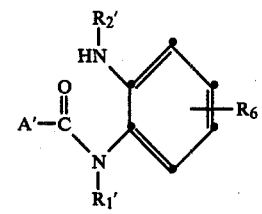

wherein A is a radical of the formula

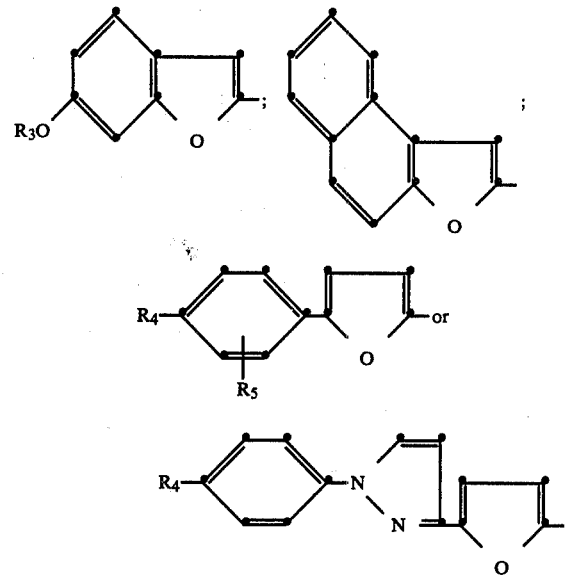

wherein $R_3$ is alkyl of 1 to 4 carbon atoms which is unsubstituted or substituted by phenyl or alkoxy of 1 to 4 carbon atoms or alkenyl of 3 or 4 carbon atoms, each of $R_4$ and $R_5$ independently is hydrogen, chlorine or methyl, each of $R_1'$ or $R_2'$ independently is alkyl of 1 to 4 carbon atoms, alkenyl of 3 or 4 carbon atoms, cyanoalkyl of 2 to 4 carbon atoms, carbamoylmethyl, alkoxycarbonylmethyl containing 1 to 3 carbon atoms in the alkoxy moiety, benzyl, hydroxyalkyl of 2 or 3 carbon atoms or phenyl, but only one of $R_1'$ and $R_2'$ can be phenyl, and $R_6$ is hydrogen, chlorine, alkyl of 1 to 4 carbon atoms, $CONY_1Y_2$ or $SO_2NY_1Y_2$ wherein $Y_1$ is hydrogen, alkyl of 1 to 4 carbon atoms, alkenyl of 3 or 4 carbon atoms, hydroxyalkyl of 2 to 4 carbon atoms, alkoxyalkyl containing a total of 3 to 6 carbon atoms, cyclohexyl or benzyl, and $Y_2$ is hydrogen, alkyl of 1 to 4 carbon atoms, or $Y_1$ and $Y_2$ together with the nitrogen atom to which they are attached can also form a morpholine ring, alkoxycarbonyl containing 2 to 5 carbon atoms or sulfophenyl ester, trifluoromethyl, alkylsulfonyl of 1 to 4 carbon atoms or arylsulfonyl.

2. A N-acyl-o-phenylenediamine according to claim 1 of the formula

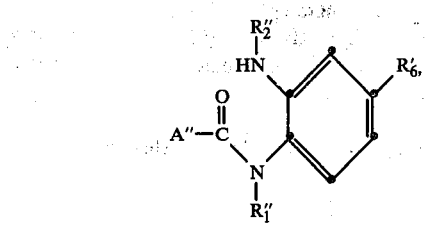

wherein A″ is a radical of the formula

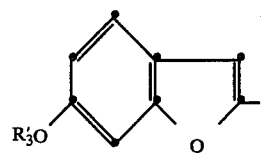

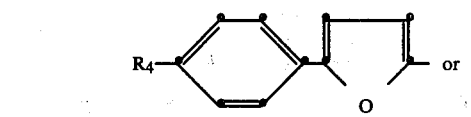

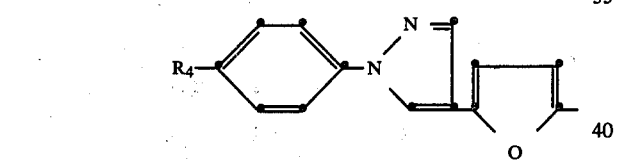

wherein $R_3'$ is alkyl of 1 to 4 carbon atoms and each of $R_4$ and $R_5$ independently is hydrogen, chlorine or methyl, each of $R_1''$ and $R_2''$ independently is alkyl of 1 to 4 carbon atoms, alkenyl of 3 or 4 carbon atoms, cyanoalkyl of 2 or 3 carbon atoms, alkoxycarbonylmethyl containing 1 to 3 carbon atoms in the alkoxy moiety, benzyl or phenyl, but only one of $R_1''$ and $R_2''$ can be phenyl, and $R_6'$ is hydrogen, methyl, chlorine, alkylsulfonyl of 1 to 4 carbon atoms, phenylsulfonyl, cyano, trifluoromethyl, phenoxysulfonyl, alkoxycarbonyl containing a total of 2 to 5 carbon atoms or $CONY_1Y_2$ or $SO_2NY_1Y_2$ wherein $Y_1$ is hydrogen, alkyl of 1 to 4 carbon atoms, alkenyl of 3 or 4 carbon atoms, hydroxyalkyl of 2 to 4 carbon atoms, alkoxyalkyl containing a total of 3 to 6 carbon atoms, cyclohexyl or benzyl, and $Y_2$ is hydrogen, alkyl of 1 to 4 carbon atoms, or $Y_1$ and $Y_2$ together with the nitrogen atom to which they are attached can also form a morpholine ring.

3. A N-acyl-o-phenylenediamine according to claim 2 of the formula

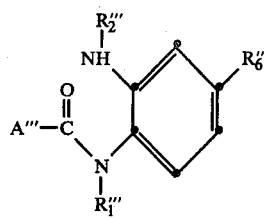

wherein A‴ is a radical of the formula

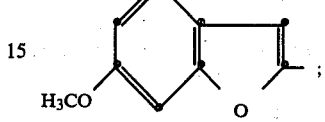

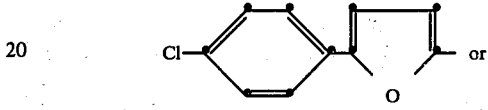

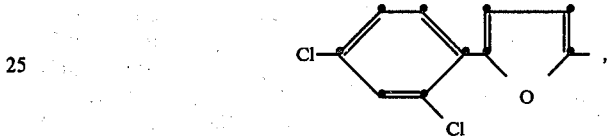

$R_1'''$ is alkyl of 1 to 4 carbon atoms, phenyl or benzyl, $R_2'''$ is alkyl of 1 to 4 carbon atoms, cyanoalkyl of 2 or 3 carbon atoms or alkoxycarbonylmethyl containing 1 to 3 carbon atoms in the alkoxy moiety, and $R_6''$ is hydrogen, alkylsulfonyl of 1 to 4 carbon atoms, phenoxysulfonyl, sulfamoyl, alkylsulfamoyl of 1 to 4 carbon atoms, alkoxycarbonyl containing 1 to 3 carbon atoms in the alkoxy moiety, or cyano.

4. A N-acyl-o-phenylenediamine according to claim 3 of the formula

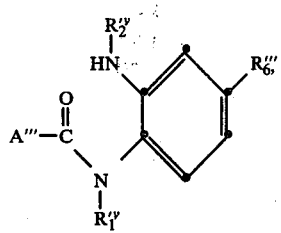

wherein A‴ is a radical of the formula

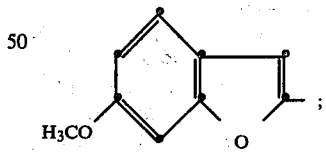

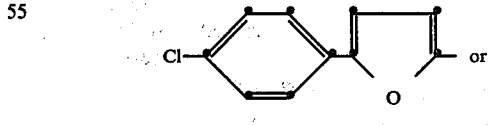

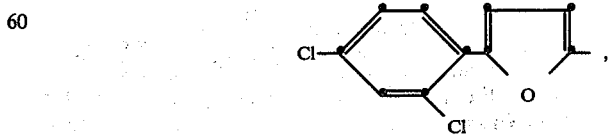

$R_1^{iv}$ is methyl or benzyl, $R_2^{iv}$ is methyl or phenyl and $R_6'''$ is hydrogen, methylsulfonyl, methylsulfamoyl or phenoxysulfonyl.

* * * * *

UNITED STATES PATENT AND TRADEMARK OFFICE
CERTIFICATE OF CORRECTION

PATENT NO. : 4,455,436
DATED : June 19, 1984
INVENTOR(S) : HANS R. MEYER et al

It is certified that error appears in the above-identified patent and that said Letters Patent is hereby corrected as shown below:

| | |
|---|---|
| Col. 3, line 45 | Correct spelling of --trifluoromethyl-- |
| Col. 4, line 63, Col. 5, line 21, Col. 6, line 62, Col. 7, line 45 and Col. 10, lines 19 and 24 | After "X" delete "⊕" and substitute --⊖-- |
| Col. 10, line 13 and Col. 10, line 50 | After "X₁" delete "⊕" and substitute --⊖-- |
| Col. 10, line 18 | Delete "14%" and substitute --40%-- |
| Col. 12, line 56 | Delete "dyeing" and substitute --dyeings-- |
| Col. 14, line 35 | Delete formula "No. (200)" and substitute |

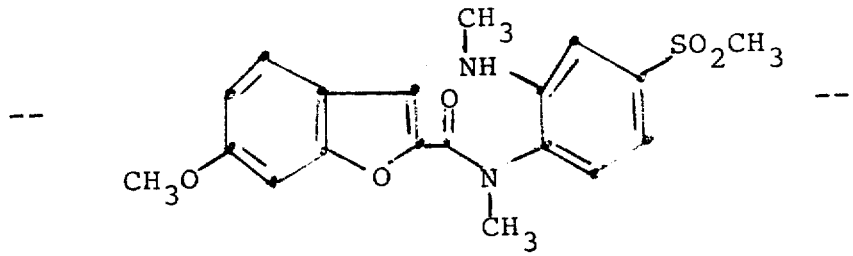

(101)

| | |
|---|---|
| Col. 12, line 64 | Delete "expecially" and substitute --especially-- |
| Col. 13, line 18 | Delete "streching" and substitute --stretching-- |

UNITED STATES PATENT AND TRADEMARK OFFICE
CERTIFICATE OF CORRECTION

PATENT NO. : 4,455,436
DATED : June 19, 1984
INVENTOR(S) : HANS R. MEYER et al

Page 2 of 2

It is certified that error appears in the above-identified patent and that said Letters Patent is hereby corrected as shown below:

Col. 14, line 55    Delete formula "No. (101)" and substitute

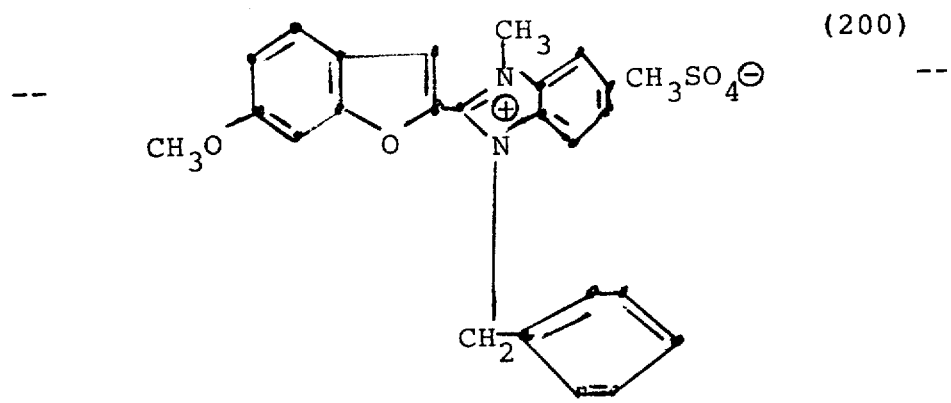

Col. 26, line 20    Delete "A'" and substitute --A--

Signed and Sealed this

Nineteenth Day of February 1985

[SEAL]

Attest:

DONALD J. QUIGG

Attesting Officer    Acting Commissioner of Patents and Trademarks